United States Patent
Ketchie et al.

(10) Patent No.: US 11,827,595 B2
(45) Date of Patent: Nov. 28, 2023

(54) ESTER SYNTHESIS USING HETEROGENEOUS AU/TIO2 CATALYST

(71) Applicant: Eastman Chemical Company, Kingsport, TN (US)

(72) Inventors: William Christopher Ketchie, Kingsport, TN (US); Sumit Chakraborty, Johnson City, TN (US); Leslie Sharon Depew, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 54 days.

(21) Appl. No.: 17/309,384

(22) PCT Filed: Nov. 12, 2019

(86) PCT No.: PCT/US2019/060816
§ 371 (c)(1),
(2) Date: May 24, 2021

(87) PCT Pub. No.: WO2020/102124
PCT Pub. Date: May 22, 2020

(65) Prior Publication Data
US 2022/0251020 A1    Aug. 11, 2022

Related U.S. Application Data

(60) Provisional application No. 62/760,306, filed on Nov. 13, 2018.

(51) Int. Cl.
*C07C 67/44* (2006.01)
*B01J 23/52* (2006.01)

(52) U.S. Cl.
CPC ............ *C07C 67/44* (2013.01); *B01J 23/52* (2013.01)

(58) Field of Classification Search
CPC ............ C07C 67/44; B01J 23/52; B01J 31/38
See application file for complete search history.

(56) References Cited

U.S. PATENT DOCUMENTS

| | | | |
|---|---|---|---|
| 3,215,712 A | 11/1965 | Hübel | |
| 5,892,102 A | 4/1999 | Mikami et al. | |
| 10,577,305 B1 | 3/2020 | Chakraborty et al. | |
| 10,590,062 B1 | 3/2020 | Chakraborty et al. | |
| 2003/0060655 A1* | 3/2003 | Hayashi | B01J 23/52 502/343 |
| 2003/0176300 A1 | 9/2003 | Kodali et al. | |
| 2010/0317824 A1 | 12/2010 | Thoen et al. | |
| 2016/0137582 A1 | 5/2016 | Frey et al. | |
| 2016/0207871 A1 | 7/2016 | Kubitschke et al. | |
| 2016/0297741 A1 | 10/2016 | Janka et al. | |
| 2019/0084914 A1* | 3/2019 | Krill | C07C 67/44 |

FOREIGN PATENT DOCUMENTS

| | | |
|---|---|---|
| EP | 2 308 824 A2 | 4/2011 |
| JP | 08-099933 A | 4/1996 |
| JP | H11-43463 A | 2/1999 |
| JP | 2001-220367 A | 8/2001 |
| WO | WO 2016/164195 A1 | 10/2016 |

OTHER PUBLICATIONS

Notification of Transmittal of the International Search Report and the Written Opinion of the International Searching Authority dated Feb. 24, 2020 received in International Application No. PCT/US2019/060816.
Yamamoto et al, "Iridium-Caralyzed Oxidative Methyl Esterification of Primary Alcohols and Diols with Methanol", The Journal of Organic Chemistry, vol. 76, No. 8, Apr. 15, 2011, pp. 2937-2941.
Co-pending U.S. Appl. No. 17/309,384, filed May 24, 2021; Ketchie et al.
Co-pending U.S. Appl. No. 16/188,930 filed Nov. 13, 2018; Chakraborty et al. (U.S. Pat. No. 10,577,305).
Office Action dated Jun. 10, 2019 received in co-pending U.S. Appl. No. 16/188,930.
Notice of Allowance dated Dec. 19, 2019 received in co-pending U.S. Appl. No. 16/188,930.
Co-pending U.S. Appl. No. 16/188,958, filed Nov. 13, 2018; Chakraborty et al.
Office Action dated Jul. 9, 2019 received in co-pending U.S. Appl. No. 16/188,958.
Office Action dated Nov. 13, 2019 received in co-pending U.S. Appl. No. 16/188,958.
Notice of Allowance dated Jun. 15, 2020 received in co-pending U.S. Appl. No. 16/188,958.
Co-pending U.S. Appl. No. 16/188,976, filed Nov. 13, 2018; Chakraborty et al. (U.S. Pat. No. 10,590,062).
Office Action dated Jun. 21, 2019 received in co-pending U.S. Appl. No. 16/188,976.
Notice of Allowance dated Dec. 20, 2019 received in co-pending U.S. Appl. No. 16/188,976.
Baldino et al.; "Transfer Hydrogenation and Hydrogenation of Commercial-Grade Aldehydes to Primary Alcohols Catalyzed by 2-(Aminomethyl)pyridine and Pincer Benzo[h] quinoline Ruthenium Complexes;" Chemcatchem; vol. 8; No. 13; 2016; pp. 2279-2288.
Blum et al.; "H-transfer catalysis with $Ru_3(Co)_{12}$;" Tetrahedron Letters; vol. 22; No. 16; Jan. 1, 1981; pp. 1541-1544.
Blum et al.; "Catalytically Reactive Ruthenium Intermediates in the Homogeneous Oxidation of Alcohols to Esters;" Israel Journal of Chemistry; vol. 24; 1984; pp. 144-148.
Blum et al.; "Catalytically Reactive ($\eta^4$-tetracyclone)$(CO)_2(H)_2$Ru and Related Complexes in Dehydrogenation of Alcohols to Esters;" Journal of Organometallic Chemistry; 1985; 282; pp. C7-C10.

(Continued)

*Primary Examiner* — Yate' K Cutliff
(74) *Attorney, Agent, or Firm* — Michael J. Blake; Tammye L. Taylor Polk

(57) ABSTRACT

A process for direct esterification of an alkyl aldehyde with an alkyl alcohol to produce an alkyl ester is disclosed. The process comprises reacting an alkyl aldehyde with an alkyl alcohol in the presence of an Au/TiOa catalyst, a base and an enal or oxygen to form an ester and an aldehyde. The process avoids liberation of water and avoids the step of oxidation of the alkyl aldehyde to an alkyl acid.

5 Claims, No Drawings

(56) References Cited

OTHER PUBLICATIONS

Blum et al.; "Structure of $\eta^4$-Ph$_4$C$_4$CO)(CO)$_3$Ru—a Catalyst Precursor in H-Transfer and Dehydrogenation Reactions of Alcohols;" Inorganica Chimica Acta; 1985; 97; pp. L25-L26.
Chakraborty et al.; "Well-Defined Iron Catalysts for the Acceptorless Reversible Dehydrogenation-Hydrogenation of Alcohols and Ketones;" ACS Catal.; 2014; 4; pp. 3994-4003.
Eberhardt et al.; "Dehydrogenative Coupling of Aldehydes with Alcohols Catalyzed by a Nickel Hydride Complex;" Organometallics; 2019; 38; pp. 1468-1478.
Funk et al.; "Synthesis and Catalytic Activity of (3,4-Diphenylcyclopentadienone) Iron Tricarbonyl Compounds in Transfer Hydrogenations and Dehydrogenations;" Organometallics; vol. 37; No. 7; Mar. 27, 2018; pp. 1133-1140.
Gianetti et al.; "Nitrous Oxide as a Hydrogen Acceptor for the Dehydrogenative Coupling of Alcohols;" Angew. Chem. Int. Ed.; 2016; 55; pp. 1854-1858.
Grigg et al.; "Oxidation of Alcohols by Transition Metal Complexes—IV;" Tetrahedron; 1981; vol. 37; No. 24; pp. 4313-4319.
Gunanathan et al.; "Applications of Acceptorless Dehydrogenation and Related Transformations in Chemical Synthesis;" Science; 2013; vol. 341; pp. 249.
Gunanathan et al.; "Direct Conversion of Alcohols to Acetals and H2 Catalyzed by an Acridine-Based Ruthenium Pincer Complex;" J. Am. Chem. Soc.; 2009; 131; pp. 3146-3147.
Johnson et al.; "(Cyclopentadienone)iron Shvo Complexes: Synthesis and Applications to Hydrogen Transfer Reactions;" Organometallics; 2013; 30; pp. 1859-1868.
Karmel et al.; "Mono(imidazoline-2-iminato) Actinide Complexes: Synthesis and Application in the Catalytic Dimerization of Aldehydes;" J. Am. Chem. Soc.; 2014; 136; pp. 17180-17192.
Khusnutdinova et al.; "Metal-Ligand Cooperation;" Angew. Chem. Int. Ed.; 2015; 54; pp. 12236-12273.
Kiran et al.; "Single-Step Conversion of Electron-Deficient Aldehydes into the Corresponding Esters in Aqueous Alcohols in the Presence of Iodine and Sodium Nitrite;" Synthesis; 2010; 2; pp. 276-282.
Kuriyama et al.; "Catalytic Hydrogenation of Esters. Development of an Efficient Catalyst and Processes for Synthesising (R)-1,2-Propanediol and 2-(/-Menthoxy)ethanol;" Org. ProcessRes. Dev.; 2012; 16; pp. 166-171.
Lee et al.; "N-Heterocyclic Carbene Catalyzed Oxidative Macrolactonization: Total Synthesis of (+)-Dactylolide;" Angew. Chem. Int. Ed.; 2012; 51; pp. 5735-5738.
Menashe et al.; "Catalytic disproportionation of aldehydes with ruthenium complexes;" Organometallics; vol. 10; No. 11; 1991; pp. 3885-3891.
Murahashi et al.; "Ruthenium-Catalyzed Oxidative Transformation of Alcohols and Aldehydes to Esters and Lactones;" J. Org. Chem.; 1987; 52; pp. 4319-4327.
Murahashi et al.; "Ruthenium Catalyzed Transformation of Alcohols to Esters and Lactones;" Tetrahedron Letters; 1981; vol. 22; No. 52; pp. 5327-5330.
Nielsen et al.; "Towards a Green Process for Bulk-Scale Synthesis of Ethyl Acetate: Efficient Acceptorless Dehydrogenation of Ethanol;" Angew. Chem. Int. Ed.; 2012; 51; pp. 5711-5713.
Notification of Transmittal of the International Search Report and the Written Opinion of the International Searching Authority dated Feb. 21, 2020 received in International Application No. PCT/US2019/060822.
Notification of Transmittal of the International Search Report and the Written Opinion of the International Searching Authority dated Feb. 27, 2020 received in International Application No. PCT/US2019/060818.
Notification of Transmittal of the International Search Report and the Written Opinion of the International Searching Authority dated Feb. 27, 2020 received in International Application No. PCT/US2019/060814.
Rueping et al.; "Asymmetric oxidative Lewis base catalysis—unifying iminium and enamine organocatalysis with oxidations;" Chem. Commun.; 2012; 48; pp. 2201-2203.
Sarkar et al.; "NHC Catalyzed Oxidations of Aldehydes to Esters: Chemoselective Acylation of Alcohols in Presence of Amines;" J. Am. Chem. Soc.; 2010; 132; pp. 1190-1191.
Spasyuk et al.; "Acceptorless Dehydrogenative Coupling of Ethanol and Hydrogenation of Esters and Imines;" Organometallics; 2012; 31; pp. 5239-5242.
Spasyuk et al.; "From Esters to Alcohols and Back with Ruthenium and Osmium Catalysts;" Angew. Chem. Int. Ed.; 2012; 51; pp. 2772-2775.
Spasyuk et al.; "Chemoselective Hydrogenation of Carbonyl Compounds and Acceptorless Dehydrogenative Coupling of Alcohols;" J. Am. Chem. Soc.; 2015; 137; pp. 3743-3746.
Srimani et al.; "Ruthenium Pincer-Catalyzed Cross-Dehydrogenative Coupling of Primary Alcohols with Secondary Alcohols under Neutral Conditions;" Adv. Synth. Catal.; 2012; 354; pp. 2403-2406.
Sumino et al.; "Carbonylation Reactions of Alkyl Iodides through the Interplay of Carbon Radicals and Pd Catalysts;" Acc. Chem. Res.; 2014; 47; pp. 1563-1574.
Thermo Fisher Scientific product page for Acros organics 5.4M (30 wt%) solution in methanol, downloaded from https://www.fishersci.com/shop/products/sodium-methoxide-5-4m-30-wt-solution-methanol-acroseal-acros-organics-2/AC428361000 on Jul. 2, 2019 (Year: 2019).
Toubiana et al.; "The true catalyst in hydrogen transfer reactions with alcohol donors in the presence of RuCl$_2$(PPh$_3$)$_3$ is ruthenium(0) nanoparticles;" Catal. Sci. Technol.; 2012; 2; pp. 1644-1653.
Trincado et al.; "Molecular catalysts for hydrogen production from alcohols;" Energy Environ. Sci.; 2014; 7; pp. 2464-2503.
Whittaker et al.; "Nickel-Catalyzed Dehydrogenative Cross-Coupling: Direct Transformation of Aldehydes into Esters and Amides;" Angew. Chem. Int. Ed.; 2015; 54; pp. 1312-1315.
Yang et al.; "New air-stable iron catalyst for efficient dynamic kinetic resolution of secondary benzylic and aliphatic alcohols;" Tetrahedron Letters; 58; 2017; pp. 2487-2489.
Yang et al.; "Substitution of alcohols by N-nucleophiles via transition metal-catalyzed dehydrogenation;" Chem. Soc. Rev.; 2015; 44; pp. 2305-2329.
Zhang et al.; "Electron-Rich PNP- and PNN-Type Ruthenium(II) Hydrido Borohydride Pincer Complexes. Synthesis, Structure, and Catalytic Dehydrogenation of Alcohols and Hydrogenation of Esters;" Organometallics; 2011; 30; pp. 5716-5724.
Zhang et al.; "Facile Conversion of Alcohols into Esters and Dihydrogen Catalyzed by New Ruthenium Complexes;" J. Am. Chem. Soc.; 2005; 127; pp. 10840-10841.

* cited by examiner

ESTER SYNTHESIS USING HETEROGENEOUS AU/TIO2 CATALYST

CROSS-REFERENCE TO RELATED APPLICATION(S)

This application is a national stage filing under 35 USC §371 of International Application Number PCT/US2019/060816, filed on, Nov. 12, 2019 which claims the benefit of the filing date to U.S. Provisional Application No. 62/760,306, filed on Nov. 13, 2018, the entire disclosures of which are incorporated by reference herein.

FIELD OF THE INVENTION

The invention generally relates to the field of organic chemistry. In particular, it relates to direct esterification of an alkyl aldehyde with an alkyl alcohol in a single reaction step. In one embodiment the invention relates to direct esterification of 2-ethylhexaldehyde with methanol in a single reaction step.

BACKGROUND OF THE INVENTION

Traditional methods for preparation of an ester involve the condensation reaction of an alcohol and acid. Such reactions are strongly equilibrium limited, requiring that the water formed during the reaction be removed to drive the reaction forward. When using light alcohols such as methanol, the separation is complicated by the low boiling point of methanol. Additionally, the use of a carboxylic acid most often requires the oxidation of an aldehyde to the corresponding acid requiring an additional processing step.

Specifically, the formation of the 2-ethylhexyl methyl ester by traditional means, requires the reaction of 2-ethylhexyl acid (2-ethyl hexanoic acid) with methanol, while driving off water. In this process, methanol is removed with the water and the methanol must subsequently be separated by energy intensive separation processes and recycled to the reactor.

A need exists for a method to directly esterify 2-ethylhexaldehyde with methanol that avoids liberation of water and avoids the oxidation step of 2-ethylhexaldehyde to 2-ethylhexyl acid. In particular, a need also exists for a method to synthesize triethylene glycol 2-ethylhexanoate (TEG-2EH) in a one-step process starting from readily available raw materials such as 2-ethylhexyl enal, 2-ethylhexaldehyde, and triethylene glycol.

The present invention addresses this need as well as others, which will become apparent from the following description and the appended claims.

SUMMARY OF THE INVENTION

The invention is as set forth in the appended claims. In one embodiment of the invention oxygen is the oxidant. In another embodiment an enal is the oxidant. The process embodiments of this invention which have $O_2$ in the reaction mixture did not require the presence of an enal and the embodiments with an enal in the reaction mixture did require the presence of $O_2$ as they each act as the $H_2$ acceptor in the respective process embodiments.

In one embodiment the invention is a process for preparing esters comprising:
a) combining an alkyl aldehyde with an alcohol to form a first mixture;
b) heating said first mixture in the presence of an $Au/TiO_2$ catalyst in the presence of a base and oxygen to form a second mixture comprising an ester and an aldehyde; and
c) recovering said ester and said aldehyde from said second mixture.

In another embodiment the invention is a process for preparing esters comprising:
a) combining an alkyl aldehyde with an enal to form a first mixture;
b) heating said mixture in the presence of an Au/TiO2 catalyst and in the presence of a base to form a second mixture comprising an ester and an aldehyde; and
c) recovering said ester and said aldehyde from said second mixture.

In another embodiment the invention is a process for preparing 2-ethylhexyl methyl ester comprising:
a) combining 2-ethylhexaldehyde with 2-ethylhexenal to form a first mixture;
b) heating said first mixture in the presence of a $Au/TiO_2$ catalyst and in the presence of an base to form a second mixture comprising methyl-2-ethylhexanoate and 2-ethylhexaldehyde; and
c) recovering said methyl-2-ethylhexanoate and 2-ethylhexaldehyde from said second mixture.

DETAILED DESCRIPTION OF THE INVENTION

As used herein the following terms have the meaning as described below:
The term "M2EH" refers to methyl-2-ethylhexanoate.
The term "TEG" refers to triethylene glycol.
The term "TEG-2EH" refers to triethylene glycol 2-ethylhexanoate.
The term "2-HEH" refers to 2-ethylhexaldehyde.
The term "MeOH" refers to methanol.
The term "2EH" refers to 2-ethylhexyl alcohol.
The term "2HEHenal" refers to 2-ethylhexyl enal.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 0 to 100 is intended to describe and include all values within the range including sub-ranges such as 0.1-99.9, 60 to 90 and 70 to 80.

It has been surprisingly discovered that a method to directly esterify an alkyl aldehyde such as 2-ethylhexyl aldehyde with an alkyl alcohol such as methanol avoids liberation of water and avoids the step of oxidation of the alkyl aldehyde such as 2-ethylhexyl aldehyde to an alkyl acid such as 2-ethylhexyl acid.

This invention utilizes a heterogenous $Au/TiO_2$ catalyst, available commercially from Strem Chemicals, Inc. The presence of low amounts of a base such as NaOH are required for the reaction to proceed. Other suitable bases include alkali/alkaline earth bases such as LiOH, KOH, Ca(OH)$_2$, and Mg(OH)$_2$, and alkali/alkaline earth methoxides such as sodium methoxide, and potassium methoxide.

The presence of an oxidant was required to accept the H$_2$ formed during the reaction. Oxidants include O$_2$ and an unsaturated species such as an enal.

In one embodiment 2-ethylhexyl enal can be utilized as the H$_2$ acceptor, subsequently forming another 2-ethylhexaldehyde molecule that was compatible with the process.

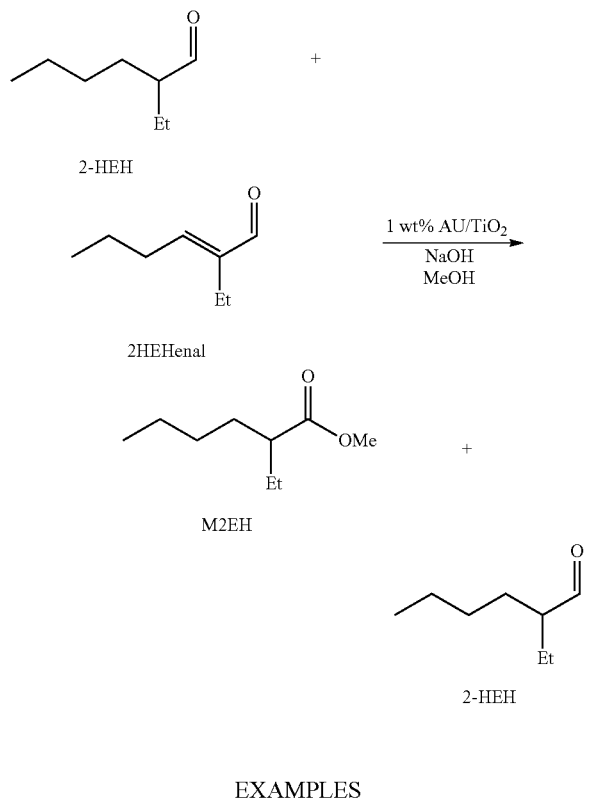

EXAMPLES

The present invention includes and expressly contemplates any and all combinations of embodiments, features, characteristics, parameters, and/or ranges disclosed herein. That is, the invention may be defined by any combination of embodiments, features, characteristics, parameters, and/or ranges mentioned herein.

This invention can be further illustrated by the following examples of preferred embodiments thereof, although it will be understood that these examples are included merely for purposes of illustration and are not intended to limit the scope of the invention unless otherwise specifically indicated.

Example 1: O$_2$ as Oxidant for the Reaction 80 g 2-ethylhexaldehyde, 50 g methanol, 3 g of 1 wt % Au/TiO2 (ground), 1 g of 50 wt % NaOH in water were placed in a 300 mL nominal Hastelloy autoclave. The reaction temperature was maintained at less than 40° C. Back-pressure was maintained at 100 psig while flowing 8 vol % O$_2$ balance N$_2$ at 2,000 sccm while stirring at 1500 RPM.

The presence of the O$_2$ (diatomic oxygen from a mixture of 8% O$_2$ in N$_2$ oxidizes the aldehyde to the acid in the solution phase. However, for the side reaction that generated the 2EH-methylester it acts as the oxidant to accept the liberated H$_2$ and formed H$_2$O resulted in a significant amount of the 2-ethylhexaldehyde reacting to form 2-ethyl hexyl acid, with approximately 5% of the 2-ethylhexaldehyde forming the desired methyl-2-ethylhexanoate product. Table 1 shows the level of methyl-2-ethylhexanoate formed as determined by Gas Chromatography (GC) as a function of reaction time. This series of reactions shows what combination of catalysts were needed to form the desired methyl ester product. It specifically shows that both the heterogeneous Au/TiO2 catalyst and solution phase base (sodium hydroxide or sodium methoxide) were needed to catalyze the formation of methylester. GC using elution times was used to determine the known species. Subsequent confirmation of speciation was confirmed by GS/Mass Spectroscopy.

TABLE 1

Methyl-2-ethylhexanoate % as function of catalyst combination and time

|  | 30 min | 60 min | 90 min | 120 min |
|---|---|---|---|---|
| Au/TiO2 | 0.23 | 0.32 | 0.30 |  |
| Au/TiO2 + NaOH | 4.03 | 5.26 | 5.52 | 5.61 |
| NaOH | 0 | 0 | 0 |  |
| Au/TiO2 + NaOMe | 2.10 | 3.26 | 3.03 | 3.25 |

Example 2: 2-ethylhexyl Enal as Oxidant for the Reaction 10 g 2-ethylhexaldehyde, 10 g 2-ethylhexyl enal, 50 g methanol, 3 g of 1 wt % Au/TiO2 (ground), 0.65 g of 50 wt % NaOH in water where added to a 150 mL titanium autoclave. The reaction temperature was maintained at 150° C. and the reactor was purged with N$_2$, then self-pressurized to about 210 psig while stirring.

Half of the starting 2-ethylhexaldehyde reacted to form the desired methyl-2-ethylhexanoate. Some of the 2-ethylhexaldehyde was hydrogenated to 2-ethylhexyl alcohol. The GC results are shown in Table 2 using elution times for the known species. Subsequent confirmation of speciation was confirmed by GC/MS.

TABLE 2

Species % as a function of time

|  | 0 min | 25 min | 80 min | 150 min | 240 min |
|---|---|---|---|---|---|
| 2HEHenal | 21.07 | 17.17 | 12.83 | 9.03 | 5.33 |
| 2-HEH | 22.75 | 22.52 | 22.91 | 23.57 | 23.57 |
| M2EH | 2.43 | 4.79 | 7.45 | 10.18 | 13.17 |
| 2EH | 2.05 | 2.88 | 3.54 | 4.28 | 5.19 |

This example shows the ability of the 2-ethylhexyl enal to act as the oxidant (H$_2$ acceptor) to drive the reaction forward. With the milder oxidant the aldehyde is not oxidized to the carboxylic acid and the enal that accepts the H$_2$ becomes an aldehyde species that can react further to the methyl ester, making the reaction a net neutral in aldehyde. This process has high atom efficiency by using the H$_2$ liberated by the methyl ester formation to hydrogenate the enal, which would normally have to be hydrogenated under high pressure $H_2$. And in the case of using $O_2$ as the oxidant, the $H_2$ liberated is lost as water. The Table 2 also shows that the reaction is not 100% selective for the enal accepting $H_2$, the aldehyde can accept the $H_2$ to form 2-ethylhexyl alcohol.

Example 2A: Determination if 2-ethylhexaldehyde is Needed for Reaction 20 g 2-ethylhexyl enal, 50 g methanol, 3 g of 1 wt % Au/TiO2 (ground), 0.65 g of 50 wt % NaOH in water where added to a 150 mL titanium autoclave. The reaction temperature was maintained at 150° C. and the reactor was purged with $N_2$, then self-pressurized to about 210 psig while stirring.

Initially no 2-ethylhexaldehyde was added and the reaction was operated for 60 min, cooled and then 10 g of 2-ethylhexaldehyde was added to the reactor, vented with $N_2$ and reheated to 150° C. to resume the reaction. While prior to introduction of 2-ethylhexaldehyde there was only trivial formation of methyl-2-ethylhexanoate, after introduction of the 2-ethylhexaldehyde the formation rate of methyl-2-ethylhexanoate was much higher, with a corresponding consumption of 2-ethylhexyl enal. Some of the 2-ethylhexaldehyde was hydrogenated to 2-ethylhexyl alcohol. The results are shown in Table 2A showing GC using elution times for the known species.

TABLE 2A

|  | 0 | 30 min | 55 min | 120 min | 160 min | 205 min | 280 min | 345 min | 425 min |
|---|---|---|---|---|---|---|---|---|---|
| 2-HEH | 0.32 | 1.28 | 1.61 | 20.53 | 20.42 | 20.92 | 21.48 | 23.42 | 26.52 |
| 2HEHenal | 44.73 | 42.55 | 42.80 | 35.76 | 33.95 | 33.53 | 32.36 | 29.54 | 24.37 |
| M2EH | 0 | 0.12 | 0.18 | 0.24 | 0.55 | 0.94 | 1.62 | 2.75 | 4.77 |

The low level of 2-ethylhexaldehyde and methyl-2-ethylhexanoate formation prior to introduction of a significant concentration of 2-ethylhexaldehyde was likely due to slow rates of hydrogen transfer reactions in which 2-ethylhexyl enal was hydrogenated, with the resulting 2-ethylhexaldehyde reacting further to methyl-2-ethylhexanoate. Upon introduction of higher concentrations (spiking) of 2-ethylhexaldehyde the desired formation of methyl-2-ethylhexanoate increased significantly. This result points to the importance of 2-ethylhexaldehyde as the reactive species in forming methyl-2-ethylhexanoate, and 2-ethylhexyl enal acting as the hydrogen acceptor which replenishes the concentration of 2-ethylhexaldehyde in the system.

Example 3: Direct Coupling Between 2-ethylhexyl Enal, 2-ethylhexaldehyde and Triethylene Glycol 20.2 g 2-ethylhexyl enal, 20.5 g 2-ethylhexaldehyde, 6 g triethylene glycol, 2 g of 1 wt % Au/TiO2 (ground), and 0.38 g of 50 wt % NaOH in water were added to a 100 mL autoseal autoclave. The reaction temperature was maintained at 185° C. and the reactor was purged with $N_2$, then self-pressurized to about 300 psig while stirring at 1000 rpm. Samples were withdrawn after every 60 minutes over a total reaction time of 6 hours. Trace amount of triethylene glycol 2-ethylhexanoate monoester (0.4 wt %) were detected by gas chromatography (GC). 2-ethylhexyl alcohol and 2-ethylhexyl acid were also detected in the mixture. No triethylene glycol 2-ethylhexanoate diester is detected.

Example 4: (Direct Coupling Between 2-ethylhexyl Enal, 2-ethylhexaldehyde and Triethylglycol 8.4 g 2-ethylhexyl enal, 8.5 g 2-ethylhexaldehyde, 40 g triethylene glycol, 2.45 g of 1 wt % Au/TiO2 (ground), and 0.51 g of 50 wt % NaOH in water where added to a 100 mL autoseal autoclave. The reaction temperature was maintained at 185° C. The reactor was purged with $N_2$, then self-pressurized to about 300 psig while stirring at 1000 rpm. Samples were withdrawn after every 60 minutes over a total reaction time of 6 hours. Trace amount of triethylene glycol 2-ethylhexanoate monoester (0.2 wt %) was detected by GC. No triethylene glycol 2-ethylhexanoate diester was detected. 2-ethylhexyl alcohol and 2-ethylhexyl acid were also detected in the mixture.

These results demonstrate the feasibility of directly coupling an aldehyde with a long chain alcohol in a single reaction step.

In the specification, there have been disclosed certain embodiments of the invention and, although specific terms are employed, they are used in a generic and descriptive sense only and not for purposes of limitation, the scope of the invention being set forth in the following claims.

We claim:

1. A process for preparing esters comprising:
   a) combining an alkyl aldehyde with an alkyl enal to form a first mixture;
   b) heating said mixture in the presence of an Au/TiO$_2$ catalyst, an alkyl alcohol and in the presence of a base to form a second mixture comprising an alkyl ester and an aldehyde; and
   c) recovering said alkyl ester and said aldehyde from said second mixture.

2. The process of claim 1 wherein said alkyl alcohol is methanol.

3. The process of claim 1 wherein said alkyl aldehyde is 2-ethylhexaldehyde.

4. The process of claim 1 wherein said alkyl enal is 2-ethylhexyl enal.

5. A process for preparing 2-ethylhexyl methyl ester comprising:
   a) combining 2-ethylhexaldehyde with 2-ethylhexenal to form a first mixture;
   b) heating said first mixture in the presence of an Au/TiO$_2$ catalyst, methanol and in the presence of a base to form a second mixture comprising methyl-2-ethylhexanoate and 2-ethylhexaldehyde; and
   c) recovering said methyl-2-ethylhexanoate and said 2-ethylhexaldehyde from said second mixture.

* * * * *